(12) United States Patent
Erdman

(10) Patent No.: US 6,541,667 B1
(45) Date of Patent: Apr. 1, 2003

(54) METHODS FOR PREPARATION OF THIOAMIDES

(75) Inventor: David T. Erdman, Liberty, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 10/023,359

(22) Filed: Dec. 17, 2001

(51) Int. Cl.⁷ ..................... C07C 327/48; C07D 249/12
(52) U.S. Cl. ...................................... 564/74; 548/263.2
(58) Field of Search ........................ 564/74; 548/263.2

(56) References Cited

U.S. PATENT DOCUMENTS

| | | | |
|---|---|---|---|
| 4,618,416 A | 10/1986 | Levesque et al. | 209/166 |
| 5,475,115 A | 12/1995 | Linker et al. | 548/263.2 |
| 5,639,891 A | 6/1997 | Linker et al. | 548/264.2 |
| 5,723,663 A | 3/1998 | Jackson et al. | 564/78 |
| 5,739,349 A | 4/1998 | Linker et al. | 548/264.6 |
| 5,874,593 A * | 2/1999 | Ushio et al. | 549/402 |
| 5,945,436 A | 8/1999 | Lai et al. | 514/357 |
| 6,077,813 A | 6/2000 | Linker et al. | |

OTHER PUBLICATIONS

Can. J. Chem., 63, (month unavailable) 1985, Khamis A. Abbas and John T. Edward, pp. 3075–3078, Effects of varying solvents and of the addition of sulfur on the rate of thiohydrolysis of aromatic nitriles.

* cited by examiner

*Primary Examiner*—Peter O'Sullivan
(74) *Attorney, Agent, or Firm*—Joseph C. Gil; Richard E. L. Henderson

(57) ABSTRACT

A process for preparing a thioamide of the formula (I)

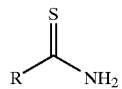

(I)

wherein R is an aryl or a heteroaryl radical includes the step of mixing a nitrile of the formula (II)

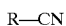

(II)

wherein R is an aryl or a heteroaryl radical with an aqueous solution comprising a sulfide and water.

21 Claims, No Drawings

METHODS FOR PREPARATION OF THIOAMIDES

FIELD OF THE INVENTION

This invention relates to processes for preparing thioamides. More particularly, the invention relates to process for preparing a thioamide of the formula (I):

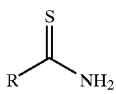
(I)

wherein R is an aryl or a heteroaryl radical. The process includes the step of mixing a nitrile with an aqueous solution comprising a sulfide and water.

BACKGROUND OF THE INVENTION

Thioamides may be used as fungicides, herbicides or as intermediates in the synthesis of thiazoles. Thioamides may also be employed as intermediates for preparing pharmaceuticals and crop protection agents.

Abbas and Edward, Can. J. Chem., 63:3075–3078 (1985) teach that thioamides may be prepared from nitriles by heating under pressure with an alcoholic solution of an alkali-metal hydrosulfide or an ammonium or substituted ammonium hydrosulfide. Abbas and Edward also teach that thioamides may be prepared by bubbling hydrogen sulfide through solutions of substituted benzonitriles in pyridine containing triethylamine.

Levesque et al., U.S. Pat. No. 4,618,416, teach thioamides can be prepared by dissolving a thioester into a solvent and adding amine.

Linker et al., U.S. Pat. Nos. 5,475,115, 5,639,891 and 5,739,349, teach that triazolinethiones can be prepared by reacting carboxylic acids with alkylthiosemicarbazides.

Linker et al., U.S. Pat. No. 6,077,813, disclose substituted aromatic thiocarboxylic acid amides and their use as herbicides. Linker et al. teach the substituted aromatic thiocarboxylic acid amides are prepared by, reacting substituted aromatic nitriles with hydrogen sulfide ($H_2S$) or with thioacetamide.

Jackson et al., U.S. Pat. No. 5,723,663, disclose a process for preparing an aliphatic thioamide which entails reacting an aliphatic nitrile with hydrogen sulfide.

Lai et al., U.S. Pat. No. 5,945,436, teach thioamides can be prepared by treating a nitrile in an inert solvent with a steady stream on hydrogen sulfide gas, catalyzed by a secondary amine.

Unfortunately, many of the prior art processes for the preparation of thioamides require the use of large amounts of hydrogen sulfide gas, and thus raise concerns regarding safety and/or difficulty of handling the gas. Many prior art processes require solvents such as dry ethanol or pyridine, and the presence of water adversely affects the reaction. Other prior art processes require that the process occur under high pressure. Thus there is a need for improved methods of preparing thioamides, particularly methods which do not require organic amines or large amounts of hydrogen sulfide gas.

SUMMARY OF THE INVENTION

Accordingly, it is an object of the present invention to obviate problems of the prior art.

It is a further object of the present invention to provide processes for the preparation of thioamides which do not require high pressures.

It is another object of the present invention to provide processes for the preparation of thioamides which do not require the use of and/or generate large quantities of hydrogen sulfide gas.

These and additional objects are provided by the processes of the present invention.

In accordance with one aspect of the invention there are provided processes for preparing a thioamide of the formula (I):

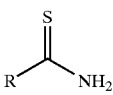
(I)

wherein R is an aryl or a heteroaryl radical, comprising the step of mixing a nitrile of the formula (II):

R—CN (II)

wherein R is an aryl or a heteroaryl radical, with an aqueous solution comprising a sulfide and water.

In accordance with another aspect of the invention there are provided processes for preparing a thioamide of the formula (I):

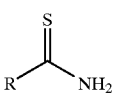
(I)

wherein R represents an aryl or a heteroaryl radical, comprising the step of reacting under pH controlled conditions a nitrile of the formula (II):

R—CN (II)

wherein R represents an aryl or a heteroaryl radical, with a compound selected from the group consisting of sodium hydrogen sulfide, potassium hydrogen sulfide, ammonium sulfide, disodium hydrogen sulfide, dipotassium hydrogen sulfide, and combinations thereof.

The processes of the invention are advantageous in that the process can occur in the presence of water, and in that handling of large quantities of hydrogen sulfide gas is avoided.

The processes of the invention are advantageous in that the process can occur without the need for high pressures.

These and additional aspects, objects and advantages of the invention are more fully described in the following detailed description.

DETAILED DESCRIPTION

Processes in accordance with the present invention comprise the step of mixing a nitrile of the formula (II):

R—CN (II)

wherein R is an aryl or a heteroaryl radical, with an aqueous solution comprising a sulfide and water to obtain a thioamide of the formula (I):

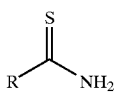

(I)

wherein R represents an aryl radical or a heteroaryl radical.

While not being bound by theory, it is believed that the nitrile reacts with a first sulfide to form a thioamide salt, and that the thioamide salt deprotonates a second sulfide and generates Na$_2$S. The reaction is believed to be as set forth in Reaction Sequence 1, below:

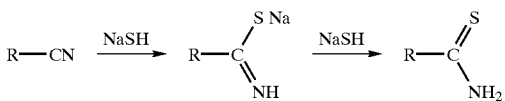

The reaction can occur in the absence of added acid, however, the slow addition of acid to the mixture of nitrile, sulfide and water is believed to assist in driving the reaction to completion.

The aryl and heteroaryl radical contain from about 5 to about 7, preferably from about 5 to about 6, atoms in the ring moiety. As used herein, "heteroaryl radical" refers to an aromatic ring comprising at least one ring atom which is other than carbon, such as a ring comprising a sulfur, oxygen or nitrogen atom. As used herein, "aryl radical" is intended to include substituted and unsubstituted aryl radicals, and "heteroaryl radical" is intended to include substituted and unsubstituted heteroaryl radicals. Suitable substituents include, but are not limited to, halogen, hydroxyl, alkyl, alkenyl, alkinyl, alkoxy, aryl, aryloxy, alkylsulphonyl, arylsulphonyl, alkanediyl, alkenediyl, alkinediyl, cycloalkanediyl, cycloalkenediyl, arenediyl, amino, cyano, isocyano, thiocyano, nitro, carboxyl, carbamoyl, thiocarbamoyl, sulpho, halogensulphonyl, alkylsulphinyl, alkylsulphonyl, alkylamino, dialkylamino, alkoxycarbonyl, dialkoxy(thio)phosphoryl, alkenyl, alkenyloxy, alkenylamino, alkylideneamino, alkenyloxycarbonyl, alkinyl, alkinyloxy, alkinylamino, alkinyloxycarbonyl, cycloalkyl, cycloalkyloxy, cycloalkylalkyl, cycloalkylalkoxy, cycloalkylideneamino, cycloalkyloxycarbonyl, cycloalkylalkoxycarbonyl, arylalkyl, arylalkoxy, aryloxycarbonyl, arylalkoxycarbonyl, heterocyclyl, heterocyclylalkyl, heterocyclylalkoxy or heterocyclylalkoxycarbonyl, and monocyclic or bicyclic, saturated or unsaturated heterocyclyl, heterocyclylamino and heterocyclylimino.

The aryl or heteroaryl radical may be substituted with fluorine, chlorine, bromine, iodine, hydroxyl, C$_{1-4}$-alkyl, C$_{3-4}$-alkenyl, C$_{3-4}$-alkinyl, C$_{1-4}$-alkoxy, phenyl, or C$_{1-4}$-alkylsulphonyl or phenylsulphonyl. The aryl or heteroaryl radical may be also be substituted with unsubstituted or substituted fluorine- or chlorine-substituted C$_{1-6}$-alkanediyl, C$_{2-6}$-alkenediyl, C$_{2-6}$-alkinediyl, C$_{3-6}$-cycloalkanediyl, C$_{3-6}$-cycloalkenediyl or phenylene; unsubstituted or halogen- or C$_{1-4}$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups; unsubstituted or halogen-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups; unsubstituted or halogen-, cyano-, carboxyl-, C$_{1-4}$-alkyl- and/or C$_{1-4}$-alkoxy-carbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups; or unsubstituted or nitro-, cyano-, carboxyl-, halogen-, C$_{1-4}$-alkyl-, C$_{1-4}$-halogenoalkyl-, C$_{1-4}$-alkyloxy-, C$_{1-4}$-halogenoalkyloxy- and/or C$_{1-4}$-alkoxycarbonyl-substituted phenyl, phenyloxy, phenyl-C1-4-alkyl, phenyl-C$_{1-4}$-alkoxy, phenyloxycarbonyl or phenyl-C$_{1-4}$-alkoxycarbonyl, (in each case optionally totally or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-C$_{1-4}$-alkyl, furyl-C$_{1-4}$-alkyl, thienyl-C$_{1-4}$-alkyl, oxazolyl-C$_{1-4}$-alkyl, isoxazole-C$_{1-4}$-alkyl, thiazole-C$_{1-4}$-alkyl, pyridinyl-C$_{1-4}$-alkyl, pyrimidinyl-C$_{1-4}$-alkyl, pyrazolylmethoxy or furylmethoxy, or represents perhydropyranylmethoxy or pyridylmethoxy.

The aryl or heteroaryl radical may be substituted with 2 moieties which together form an alkanediyl or alkenediyl group having in each case up to 4 carbon atoms which optionally contains at the beginning (or end) or within the hydrocarbon chain an oxygen atom, a sulphur atom, an SO$_2$ group, an NH group, an N—C$_{1-4}$-alkyl group, a carbonyl group and/or a thiocarbonyl group. Further, the aryl or heteroaryl radical may be substituted with a monocyclic or bicyclic, saturated or unsaturated heterocyclyl, heterocyclylamino or heterocyclylimino having in each case 2 to 6 carbon atoms and 1 to 4 nitrogen atoms in the heterocyclic ring system, which optionally contains an oxygen atom or sulphur atom and from zero to three, in one embodiment one to three, substituents selected from the group consisting of —CO—, —CS—, —SO— and/or —SO$_2$—, and which is unsubstituted or substituted by one or more substituents selected from the group consisting of nitro, hydroxyl, amino, cyano, carboxyl, carbamoyl, thiocarbamoyl, halogen, C$_{1-6}$-alkyl (which may be unsubstituted or substituted by halogen or C$_{1-4}$-alkoxy), C$_{2-6}$-alkenyl or C$_{2-6}$-alkinyl (each which may be unsubstituted or substituted by halogen), C$_{1-6}$-alkoxy or C$_{1-6}$-alkoxy-carbonyl (each which may be unsubstituted or substituted by halogen or C$_{1-4}$-alkoxy), C$_{2-6}$-alkenyloxy or C$_{2-6}$-alkinyloxy (each which may be unsubstituted or substituted by halogen), C$_{2-6}$-alkylthio, C$_{2-6}$-alkenylthio or C$_{2-6}$-alkinylthio (each which may be unsubstituted or substituted by halogen), C$_{1-6}$-alkylamino or di-(C$_{1-4}$-alkyl)-amino, C$_{3-6}$-cycloalkyl or C$_{3-6}$-cycloalkyl-C$_{1-4}$-alkyl (each which may be unsubstituted or substituted by halogen and/or C$_{1-4}$-alkyl), phenyl, phenoxy, phenylthio, phenylsulphinyl, phenylsulphonyl or phenylamino (each which may be unsubstituted or substituted by nitro, cyano, halogen, C$_{1-4}$-alkyl, C$_{1-4}$-halogenoalkyl, C$_{1-4}$-alkyloxy, C$_{1-4}$-halogenoalkyloxy and/or C$_{1-4}$-alkoxy-carbonyl).

In one embodiment the nitrile is potassium 2-(2-fluoro-4-cyano-5-ethylsulfonylaimino-phenyl)-4-methyl-5-trifluoromethyl-2,4-dihydro-3H-1,2,4-triazol-3-one, while in another embodiment the nitrile in benzonitrile. Other nitriles suitable for use herein include those set forth in Linker et al., U.S. Pat. No. 6,077,813, incorporated herein by reference.

The reaction mixture is controlled to within a pH range such that the generation of large quantities of hydrogen sulfide (H$_2$S) gas is avoided. The pressures of the H$_2$S gas over the reaction mixture is typically less than atmosphere Typically the pH is maintained in a range sufficient to result in a conversion of more than about 50%, preferably more than about 90%, by weight, of the nitrile. While not being bound by theory, it is believed that controlling the pH drives the reaction equilibrium. In one embodiment of the invention the pH of the reaction mixture is maintained at a pH no greater than about 10, preferably no greater than about 8. In another embodiment the pH is maintained in a range of from about 6 to about 10, preferably from about 7 to about 8.

Typically the pH of the reaction mixture is controlled by addition of an acid. The acid may be an organic or inorganic acid. Suitable acids include hydrochloric acid, acetic acid and sulfuric acid, preferably the acid is hydrochloric acid. In one embodiment the acid is an aqueous solution of from about 5% to about 37%, preferably from about 35% to about 37%, by weight, hydrochloric acid. In one embodiment the acid is added over a period of time of from about 1 to about 6, preferably from about 2 to about 4 hours.

Suitable sulfides may be selected from the group consisting of alkali metal hydrogen sulfides and ammonium and substituted ammonium sulfides. In one embodiment the sulfide is selected from the group consisting of sodium hydrogen sulfide, potassium hydrogen sulfide, ammonium sulfide, disodium hydrogen sulfide, dipotassium hydrogen sulfide, and combinations thereof. In one embodiment the sulfide is sodium hydrogen sulfide. The weight ratio of sulfide to nitrile is in the range of from about 1:1 to about 10:1, preferably in the range of from about 2:1 to about 5:1.

The sulfide used in the reaction is generally in the form of a solution comprising the sulfide and water, for example, the sulfide may be present in the aqueous sulfide solution at a level of from about 10% to about 30%, preferably from about 25% to about 30%, by weight of solution. The reaction may be carried out in the presence of an additional solvent other than the water present in the sulfide solution.

In one embodiment the reaction solvent is a mixture of an organic solvent and an aqueous solvent. In one embodiment of the invention the volume ratio of total aqueous solvent to total organic solvent is from about 1:0 to 1:20, preferably from about 1:1 to about 1:4; the total aqueous solvent includes water present in the aqueous sulfide solution. Suitable aqueous solvents include water and buffered aqueous solutions, preferably the aqueous solvent is water. Suitable organic solvents include toluene, benzene, xylenes, cumene, butanol and combinations thereof, preferably the organic solvent is butanol. In one preferred embodiment the solvent is a mixture of butanol and water.

A reaction catalyst may be added to the reaction mixture. Suitable reaction catalysts include sulfur and phase transfer catalysts such as quaternary ammonium salts. In one embodiment the catalyst is sulfur. The sulfur may be present in an amount of from about 1 weight % to about 30 weight %, preferably about 5 weight % to about 10 weight %, based on weight of nitrile. In another embodiment the reaction is carried out in the presence of a quaternary ammonium phase transfer catalyst, such as ALIQUAT® 336 (tricapryl methyl ammonium chloride). In yet another embodiment the reaction is carried out in the presence of both sulfur and a phase transfer catalyst.

The reaction mixture is heated at a temperature and for a time sufficient for the desired reaction to occur. Generally the temperature is no greater than about 100° C. In one embodiment the reaction is carried out at a temperature of from about 0° C. to about 100° C., preferably from about 25° C. to about 80° C. The reaction mixture is maintained at a pressure under which the desired reaction will occur, typically a pressure of less than about 1.2 bar absolute. In one embodiment the reaction occurs at a pressure no greater than about 1 bar absolute, while in another embodiment the reaction occurs at a pressure of from about 0.9 to about 1.01, preferably about 1, bar absolute.

The reaction does not require the presence of added secondary or tertiary amines. As used herein, "added secondary or tertiary amines" refers to secondary and tertiary amines added to the reaction mixture, and does not include any secondary or tertiary amines formed as intermediates during the preparation of the thioamide. In one embodiment the reaction mixture is substantially free of, preferably free of, added secondary or tertiary amines.

Throughout the examples and the present specification, parts and percentage, are by weight unless otherwise specified. The following example is illustrative only and is not intended to limit the scope of the methods of the invention as defined by the claims.

EXAMPLES

Example 1

About 10 g (about 0.1 mole) benzonitrile and abut 30 g of a 29%, by weight, aqueous solution of sodium hydrogen sulfide (about 0.16 mole of NaHS) and about 2 g of sulfur are added to about 50 ml of butanol and the resulting mixture is heated to about 90° C. for about 3 hours. Then about 36 g of 10% HCl is added slowly over a time period of from about 4 to about 5 hours.

A mixture comprising an aqueous phase and an organic phase is formed, and the phases are separated while still hot. The organic phase is cooled, and a seed crystal added to encourage crystallization. The resulting yellow solids are filtered, washed with water, and then washed with butanol. The yield is about 70%, the AI (active ingredient) is greater than about 95%, and the melting point of the solids is in the range of from about 115° C. to about 117° C.

Example 2

About 50 g (about 0.11 mole) of potassium 2-(2-fluoro-4-cyano-5-ethylsulfonylamino-phenyl)-4-methyl-5-trifluoromethyl-2,4-dihydro-3H-1,2,4-triazol-3-one, about 5 g of sulfur, and about 87 g of a 29%, by weight, aqueous solution of sodium hydrogen sulfide (about 0.45 mole of NaHS) are added to about 250 ml of butanol and the resulting mixture is heated to about 80° C. for about 1 hour. Then about 29 g of 37% HCl is added slow y over a time period of about 4 hours.

A mixture comprising an aqueous phase and an organic phase is formed. The mixture is cooled to room temperature and the phases are separated. The organic phase is made acidic with 10% HCl, and a seed crystal added to encourage crystallization. The product is collected by filtration. The yield is about 70%, the AI (active ingredient) is greater than about 98%.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

What is claimed is:

1. A process for preparing a thioamide of the formula (I)

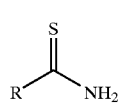

(I)

wherein R is an aryl or a heteroaryl radical, comprising the step of mixing a nitrile of the formula (II)

R—CN (II)

wherein R is an aryl or a heteroaryl radical,
with an aqueous solution comprising (i) a sulfide selected from the group consisting of sodium hydrogen sulfide, potassium hydrogen sulfide, ammonium sulfide, disodium hydrogen sulfide, dipotassium hydrogen sulfide, and combinations thereof and (ii) water.

2. The process of claim 1 wherein the pH of the reaction mixture is maintained in the range of from about 6 to about 10.

3. A process according to claim 1, wherein the step of mixing the nitrile and the aqueous solution forms a reaction mixture, and the process further comprises the step of adding an acid to the reaction mixture.

4. The process of claim 3, wherein the acid is selected from the group consisting of hydrochloric acid, acetic acid and sulfuric acid.

5. A process according to claim 2, wherein the weight ratio of sulfide to nitrile is in the range of from about 1:1 to about 10:1.

6. A process according to claim 1, wherein the aqueous solution further comprises an organic solvent.

7. The process of claim 6, wherein the organic solvent is selected from the group consisting of toluene and butanol.

8. A process according to claim 1, wherein the step of mixing a nitrile with the aqueous solution occurs in the presence of a reaction catalyst.

9. A process according to claim 8, wherein the reaction catalyst is sulfur.

10. A process for preparing a thioamide of the formula (I)

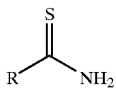
(I)

wherein R represents an aryl or a heteroaryl radical, comprising the step of reacting under pH controlled conditions a nitrile of the formula (II)

R—CN (II)

wherein R is as defined above, with a compound selected from the group consisting of sodium hydrogen sulfide, potassium hydrogen sulfide, ammonium sulfide, disodium hydrogen sulfide, dipotassium hydrogen sulfide, and combinations thereof.

11. The process of claim 10 wherein the reaction is carried out in the presence of a reaction solvent.

12. The process of claim 11 wherein the reaction solvent is water.

13. The process of claim 11 wherein the reaction solvent is a mixture of an organic solvent and an aqueous solvent.

14. The process of claim 13 wherein the ratio of aqueous solvent to organic solvent is from about 1:0 to 1:20.

15. The process of claim 13 wherein the organic solvent is selected from the group consisting of toluene and butanol and the aqueous solvent is water.

16. The process of claim 10 wherein the reaction is carried out at a temperature of from about 0° C. to about 100° C.

17. The process of claim 10 wherein the pH of the reaction mixture is controlled by addition of an acid.

18. The process of claim 11 wherein the acid is selected from the group consisting of hydrochloric acid, acetic acid and sulfuric acid.

19. The princess of claim 10 wherein the pH of the reaction mixture is maintained in the range of from about 6 to about 10.

20. The process of claim 1 further comprising the step of adding a catalyst selected from the group consisting of quaternary ammonium compounds and combinations thereof to the reaction mixture.

21. The process of claim 10 wherein the nitrile is potassium 2-(2-fluoro-4-cyano-5-ethylsulfonylamino-phenyl)-4-methyl-5-trifluoromethyl-2,4-dihydro-3H-1,2,4-triazol-3-one.

* * * * *